(12) United States Patent
Evans et al.

(10) Patent No.: US 9,889,281 B2
(45) Date of Patent: Feb. 13, 2018

(54) CELL ENCAPSULATION LOADING DEVICE

(71) Applicant: Janssen Biotech, Inc., Horsham, PA (US)

(72) Inventors: Stephen Evans, Westwood, MA (US); Audrey Bell, Newton, MA (US)

(73) Assignee: Janssen Biotech, Inc., Horsham, PA (US)

( * ) Notice: Subject to any disclaimer, the term of this patent is extended or adjusted under 35 U.S.C. 154(b) by 28 days.

(21) Appl. No.: 15/047,027

(22) Filed: Feb. 18, 2016

(65) Prior Publication Data

US 2016/0243344 A1   Aug. 25, 2016

Related U.S. Application Data

(60) Provisional application No. 62/117,974, filed on Feb. 19, 2015.

(51) Int. Cl.
*A61M 31/00* (2006.01)
*C12M 1/12* (2006.01)
*C12M 1/00* (2006.01)

(52) U.S. Cl.
CPC ......... *A61M 31/00* (2013.01); *A61M 2202/09* (2013.01); *A61M 2209/045* (2013.01); *C12M 1/00* (2013.01); *C12M 1/12* (2013.01)

(58) Field of Classification Search
CPC ........ A61M 2209/045; A61M 2202/09; A61M 31/00; A61M 31/002; A61J 1/20; A61J 1/2089; A61J 1/2096; B65D 90/58; B65D 90/587; C12M 1/12; C12M 1/16; C12M 23/28; C12M 23/38; C12M 23/42

USPC ........................................................... 251/37
See application file for complete search history.

(56) References Cited

U.S. PATENT DOCUMENTS

| | | | |
|---|---|---|---|
| 3,886,047 A * | 5/1975 | Billups, Jr. ............ | C12M 23/10 220/319 |
| 4,456,026 A * | 6/1984 | Kantor .................. | F16K 3/0227 137/315.29 |
| 5,292,515 A | 3/1994 | Moro et al. | |
| 5,672,505 A * | 9/1997 | Jones ..................... | C12M 23/08 422/561 |
| 5,686,301 A * | 11/1997 | Falkenberg ............ | C12M 23/24 422/552 |
| 5,702,945 A * | 12/1997 | Nagels .................... | A61F 2/062 435/297.1 |
| 5,902,745 A | 5/1999 | Butler et al. | |
| 5,964,261 A | 10/1999 | Neuenfeldt et al. | |
| 8,317,799 B2 | 11/2012 | Schon et al. | |
| 2008/0268422 A1 * | 10/2008 | Olivier .................... | C12M 1/12 435/4 |

(Continued)

FOREIGN PATENT DOCUMENTS

| WO | WO 2015056986 A1 * | 4/2015 | ............ C12M 23/10 |
|---|---|---|---|
| WO | WO 2016/134101 A1 | 8/2016 | |
| WO | WO 2016/134101 R | 8/2016 | |

*Primary Examiner* — Timothy L Maust
*Assistant Examiner* — Andrew Stclair
(74) *Attorney, Agent, or Firm* — Lois A. Gianneschi

(57) ABSTRACT

The present invention provides a loading fixture for loading cells, cell clusters, and media to an immune-isolation device. The loading fixture permits the loading of cells into the immune-isolation device without manual manipulation of the immune-isolation device, until the loading device is opened at the point of use, thereby minimizing the risk of contamination of the immune-isolation device.

22 Claims, 20 Drawing Sheets

(56) References Cited

U.S. PATENT DOCUMENTS

2014/0236078 A1 8/2014 Dalton
2014/0345748 A1* 11/2014 Rogers .................. B01L 1/02
 141/311 R

* cited by examiner

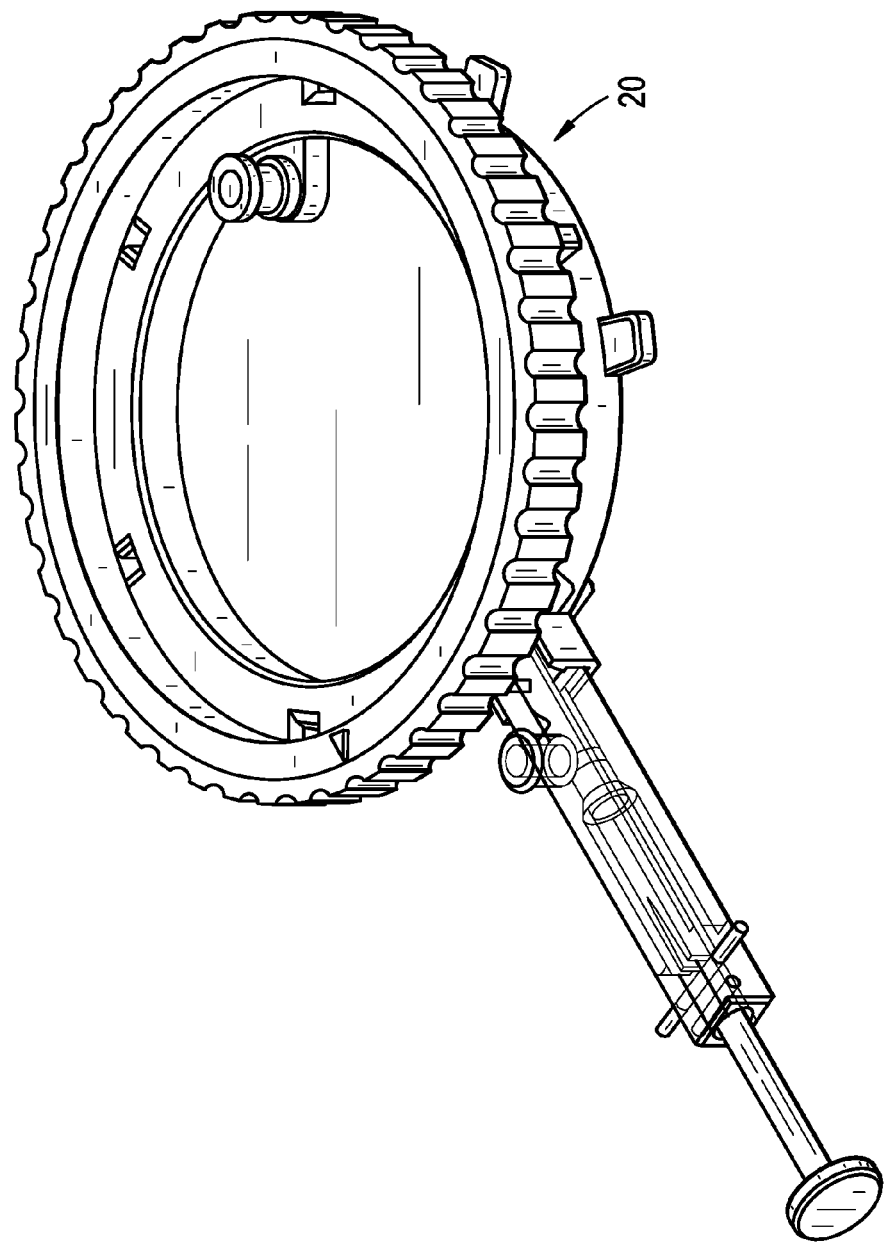

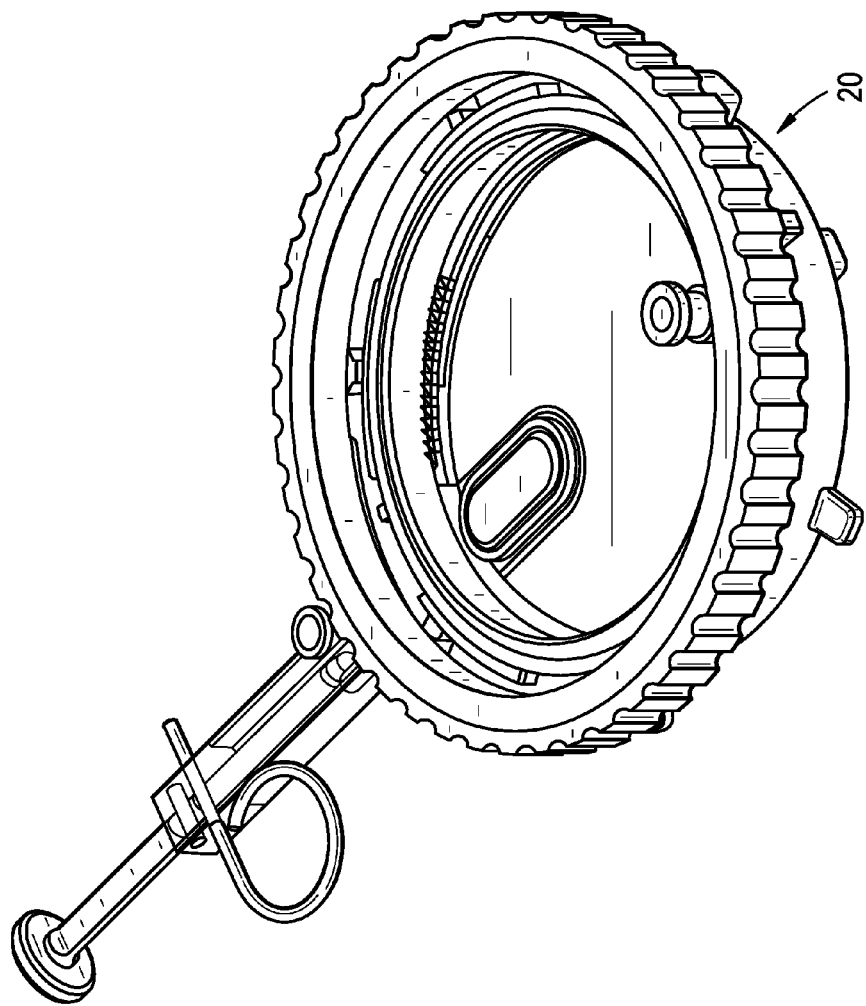

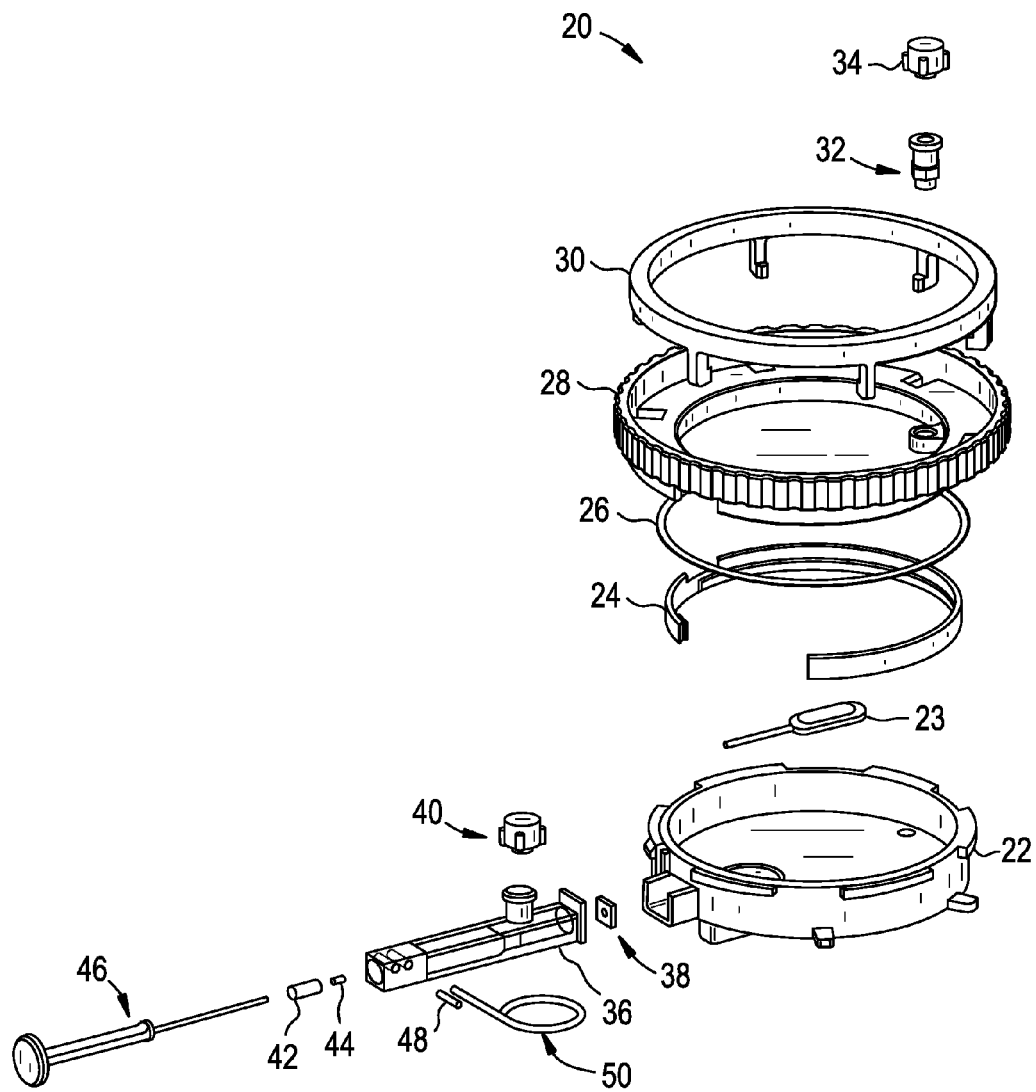

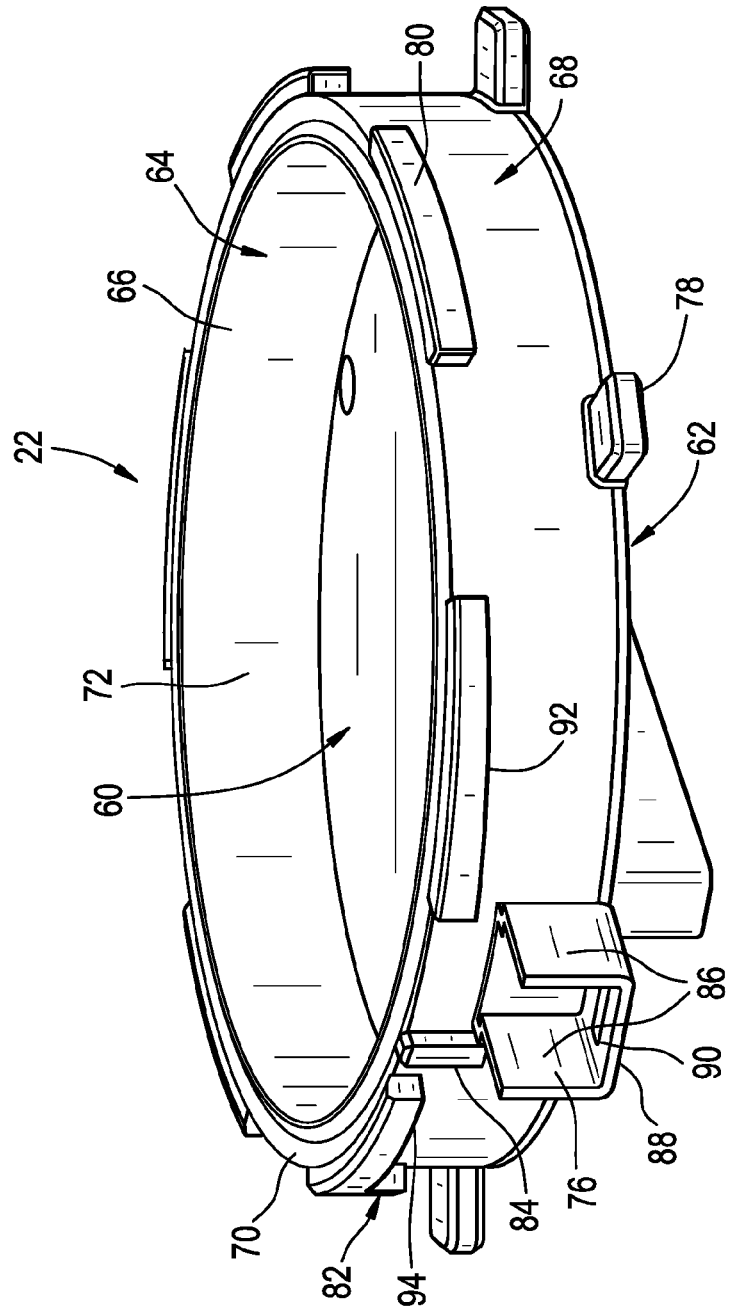

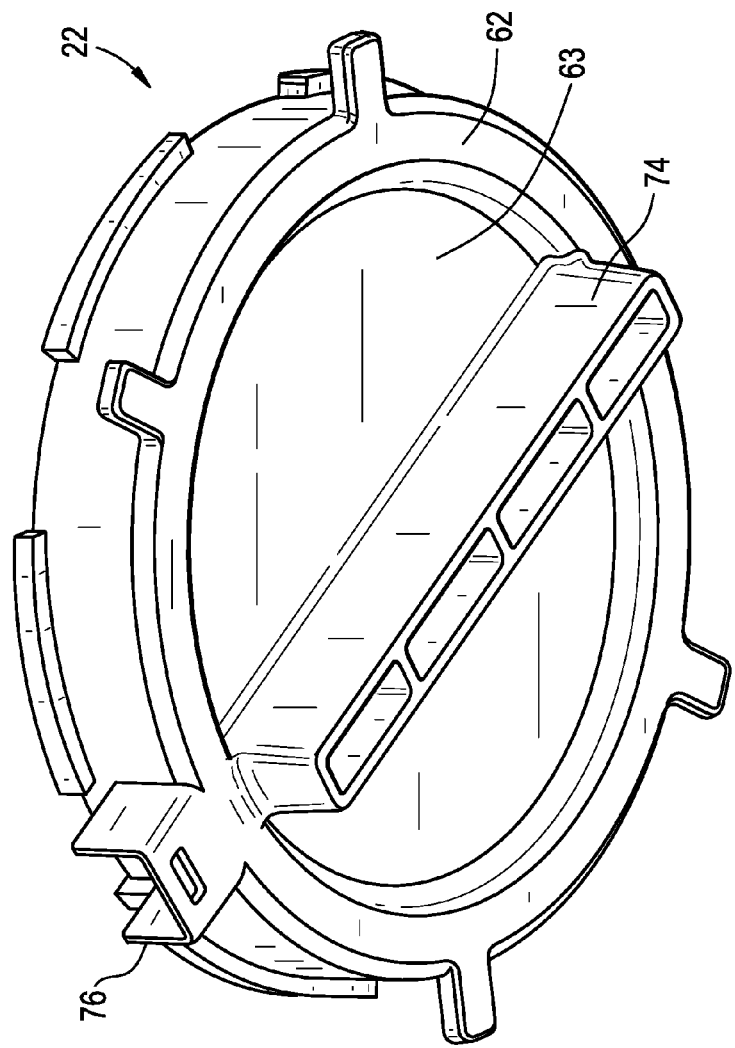

CELL ENCAPSULATION LOADING DEVICE

CROSS REFERENCE TO RELATED APPLICATION

The present application claims the benefit of U.S. Provisional Patent Application Ser. No. 62/117,974, filed Feb. 19, 2015, which is incorporated herein by reference in its entirety for all purpose.

FIELD OF THE INVENTION

The invention relates to the field of loading devices useful in loading cells into an encapsulation device. In particular, the invention relates to devices for loading cells into a medical device that will be implanted into a body.

BACKGROUND

There is a clinical need for devices that encapsulate living cells and allow transplantation into a host without triggering a robust immune response from the host. In general, cellular material harvested from one animal and implanted in another, even of the same species, will be attacked and destroyed by the host's immune response. In the case of organ transplants, immunosuppressive drugs are needed to prevent organ rejection. Otherwise, organ and tissue transplantation would almost always cause an immune response and result in destruction of the transplanted tissue.

However, it is possible to construct a device to encapsulate tissue or cells to eliminate the need for immunosuppressive drugs. Such a device typically is constructed of porous material allowing for the necessary exchange of metabolites, nutrients and waste products between the cell and the host. At the same time, the porosity of the material is controlled to isolate the interior of the device from invasion from the host immune system, including phagocytes.

After the device is loaded with living cells, it is implanted into a host body. It is important that the vasculature of the host grows into intimate contact with the exterior surface of the device so that blood vessels can facilitate the exchange of metabolites with the encapsulated cells through perfusion. The transplanted living cells must be in close proximity to the host blood vessels to ensure their continued survival and functioning. Therefore, loading of the cells within the device so that the cells are in proximity to the blood vessels is of primary importance. Additionally, loading of the cells must be carried out in a manner that minimizes trauma to the cells so that therapeutic amounts of the cells survive loading into the device.

Another factor to be considered in cell loading is that, in current practices, significant manual manipulation of the immune-isolation device ("IID") in an "open" sterile environment using aseptic sterile techniques is required. Although this open air environment is sterile, manual manipulation of the IID under these conditions is undesirable due to the increased risk of contamination by unwanted microorganisms.

Therefore, there is a need for a loading fixture and method for loading that ensures the desired placement of the cells within the device and minimizes trauma to the cells while reducing or substantially eliminating the manual manipulation of the IID thereby reducing the risk of contamination of the implantable device.

SUMMARY

In one embodiment, the invention provides a loading device comprising a base, a disk lid, having a luer adapter fixedly attached thereto, a snap lid, wherein the disk lid and snap lid form a cavity in the base, a blade ring assembly slidably connected to the base, a junction block fixedly attached to the base and having a luer adapter fixedly attached thereto, and a barb, and a barb pusher slideably connected therein.

In some embodiments, the loading device further comprises an immune-isolation device having an inlet tube and a cell pouch inserted within the cavity wherein the cell pouch rests on the base and the inlet tube is inserted through the junction block.

In other embodiments, the invention provides for methods of using the loading device comprising: (a) providing a loading device comprising a base, a disk lid, having a luer adapter fixedly attached thereto, a snap lid, wherein the disk lid and snap lid form a cavity in the base, a blade ring assembly slidably connected to the base, a junction block fixedly attached to the base and having a luer adapter fixedly attached thereto, a barb, and a barb pusher slideably connected therein, and an immune-isolation device comprising an inlet tube and a cell pouch inserted within the cavity wherein the cell pouch rests on the base and the inlet tube is inserted through the junction block; (b) sterilizing the loading device, optionally, wetting the cell pouch with hydrophilic liquid; (c) filling the cell pouch with cells and the cavity with cell media; (d) sealing the inlet tube with the barb; (d) closing the loading device; (e) transporting the loading device to the point of use; (f) opening the loading by rotating the disk lid counter-clockwise, thereby cutting the inlet tube; and (g) removing the cell pouch from the loading device at the point of use.

In another embodiment, the invention provides for a system for loading immune-isolation devices comprising: a base having a base bottom surface and a base wall extending from the base bottom surface to form a cavity; an inlet conduit positioned on the base and extending there through into the cavity of the base; a disk lid removably attachable to the base to seal the cavity; and a blade having an edge slidably disposed within the cavity of the base, whereby the edge of the blade is configured to slide in front of the inlet conduit, and whereby the system is configured to be vented.

In yet another embodiment, the invention provides for a method of preparing immune-isolation devices comprising: (a) providing a loading system comprising a base having a base bottom surface and a base wall extending from the base bottom surface to form a cavity, an inlet conduit positioned on the base and extending there through into the cavity, and a disk lid removably attachable to the base to seal the cavity; (b) coupling an immune-isolation device, comprising an inlet tube attached to a pouch, to the inlet conduit positioned on the base within the cavity; (c) sealing the cavity with the disk lid; (d) filling the pouch of the immune-isolation device with cells via the inlet conduit; (e) filling the cavity with cell media; and (f) sealing the inlet tube.

BRIEF DESCRIPTION OF THE DRAWINGS

FIG. 1A is a top perspective view of a loading device of the invention.

FIG. 1C is an alternative top perspective view of the loading device and IID of FIG. 1B.

FIG. 2B is an exploded view of the loading device of FIG. 1B.

FIG. 3 is a side perspective view of a base of the loading device of FIG. 1A.

FIG. 4 is a bottom perspective view of the base of FIG. 3.

DETAILED DESCRIPTION OF THE INVENTION

The following detailed description of the invention will be better understood when read in conjunction with the appended figures. For the purpose of illustrating the invention, the figures demonstrate embodiments of the present invention. However, the invention is not limited to the precise arrangements, examples, and instrumentalities shown.

The terms "proximal" and "distal" are used herein when describing the orientation of parts or components in relationship to one another. For the purposes of this disclosure, the proximal side is the side closest to the plunger 182 of the barb pusher assembly 46 (see FIG. 12) and the distal side is the furthest from the plunger 182 of the barb pusher assembly 46 (see FIG. 12), when the loading device 20 is in an assembled configuration (see FIGS. 1A-1C and 2A-2B).

Figure 1B:
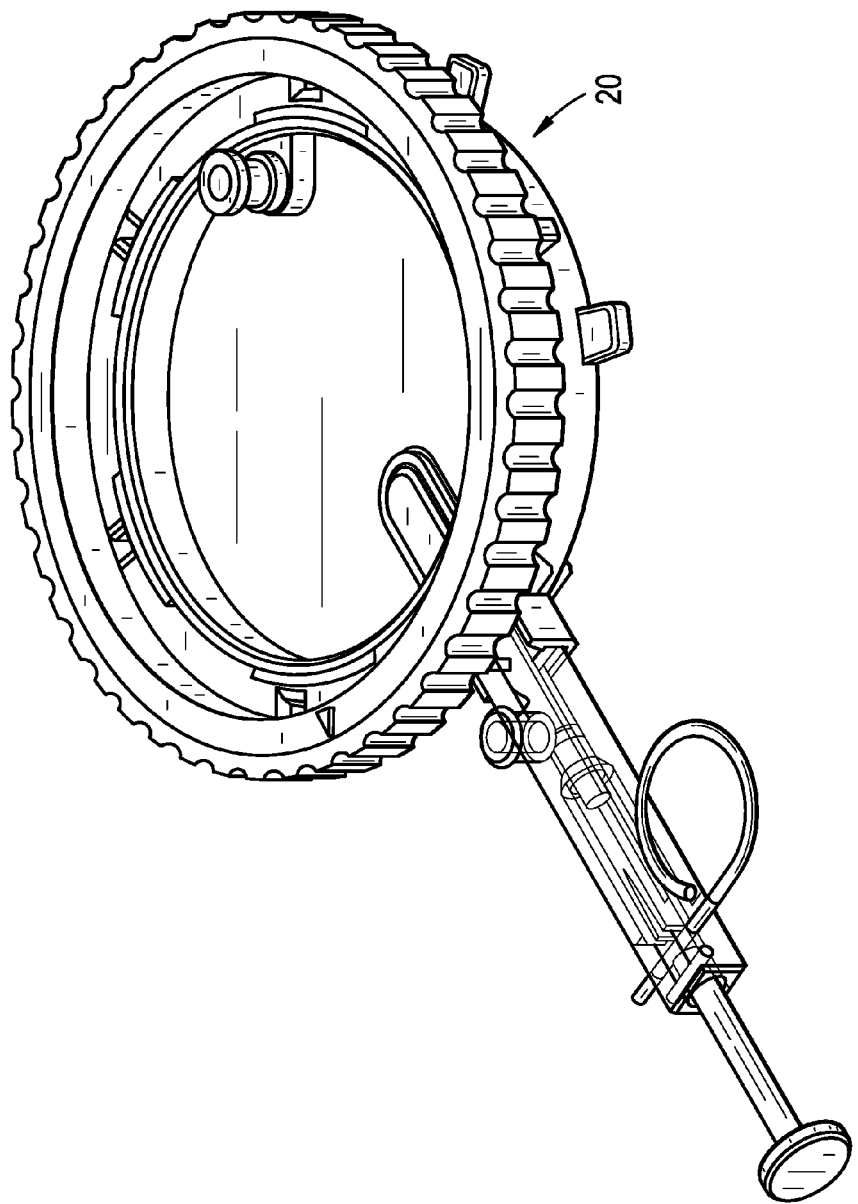
FIG. 1B is a top perspective view of the loading device of FIG. 1A with an exemplary immune-isolation device ("IID").
Figure 2A:
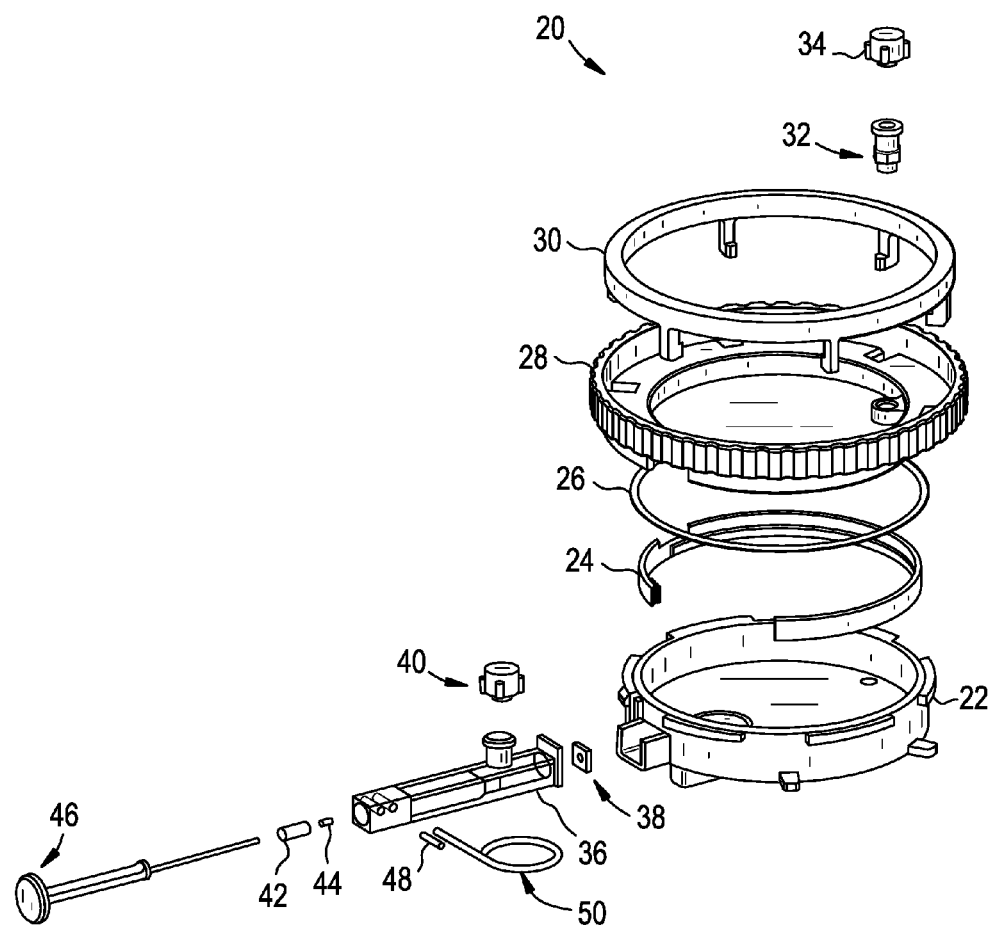
FIG. 2A is an exploded view of the loading device of FIG. 1A.

Shown in FIG. 1A is a loading device 20 of the invention. The device of the invention enables the user to load cells or cell clusters into an immune-isolation device ("IID") 23 (FIG. 2B) held within device 20 (see also FIGS. 1B and 1C). The IID 23 is an implantable medical device that allows therapeutic cell products out of the device and simultaneously protects the cells or cell clusters within the device from the host's immune response. The device of the invention enables the user to load cells or cell clusters into the IID 23 while minimizing the opportunities for contamination due to manual manipulation, minimizing cell trauma, and facilitating accurate placement of the cells within the device. Furthermore, the loading device 20 also may serve as the packaging for transport and storage of the IID 23. The IID 23 preferably is not removed from the loading device 20 until the point of use, for example when the IID 23 in the loading device 20 arrives in the surgical suite and is ready for implantation. In a preferred embodiment, the loading device 20 allows a user to: wet the IID 23 with a hydrophilic liquid, rinse or soak the IID 23 in a aqueous solution to remove residual hydrophilic liquid, load cells or cell clusters into the IID 23, surround the IID 23 loaded with cells with media enabling the cells to survive for a period of time, seal the IID 23, and finally open the loading device 20 at the point of use without tools to retrieve the IID 23, all while maintaining sterility and reducing the risk of contamination.

An embodiment of the loading device 20 is shown in FIGS. 1A-1C and 2A-2B. Loading device 20 includes a base 22 that is moveably connected to blade ring assembly 24. O-ring 26 is seated between base 22 and disk lid 28. A snap lid 30 is removably connected through disk lid 28 and furthermore, snap lid 30 is removably attached to base 22 and, with O-ring 26, forms a seal between disk lid 28 and base 22. Disk lid 28 interacts ratchetedly with blade ring assembly 24 when rotated in the clockwise direction and locked with blade ring assembly 24 when rotated in the counter-clockwise direction. First luer fitting 32, with a first luer cap 34 removably seated thereon, is fixedly attached to the top surface of disk lid 28.

Figure 10:
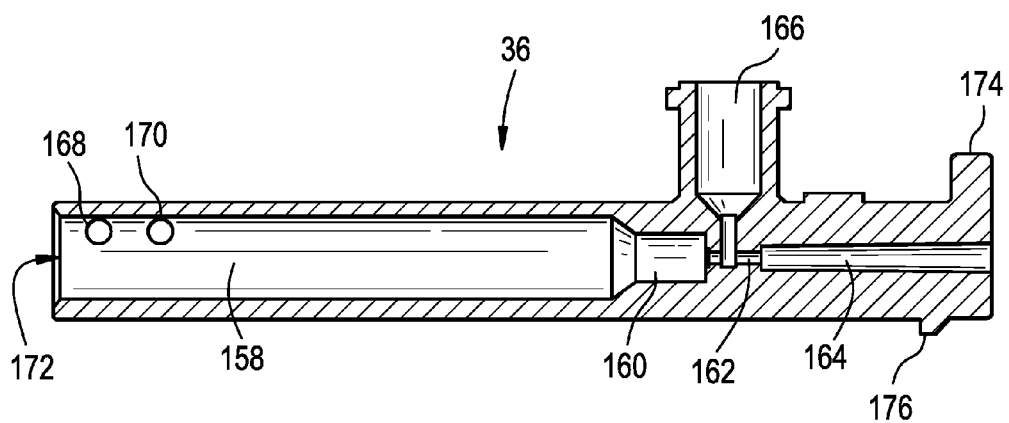
FIG. 10 is a side view of a junction block of the device of FIG. 1A.

Loading device 20 also includes junction block 36 fixedly attached to base 22. There are two tabs located at the distal end of the junction block 36. The locking tab 174 is on the top side of the junction block 36 and extends upwardly. The latch tab 176 is on the bottom side of the junction block 36 and extends downwardly as shown in FIG. 10. Latch tab 176 is inserted into notch 90 in flange base 88 (see FIG. 3) and locking tab 174 is secured by the junction block retention feature 142 on disk lid 28 (see FIG. 8). Junction block seal 38 forms a compression seal between junction block 36 and base 22 thereby preventing fluids from leaking out from between the junction block 36 and the base 22. Second luer cap 40 is removably attached to the second luer fitting 166 on junction block 36. Barb 44 is removably seated within barb plug 42 and barb plug 42 is removably seated within junction block 36. The barb plug 42 forms a compression seal against the interior of the junction block 36 on the outside of the barb plug 42 and against the barb 44 on the inside of the barb plug 42, thereby preventing fluids that are exiting or entering the loading device 20 through the second luer fitting 166 on the junction block 36 from leaking into the junction block 36. Barb pusher assembly 46 is movably inserted within junction block 36 and held in place by retainer pin 48 and safety pin 50. Retainer pin 48 prevents the barb pusher assembly 46 from coming out of the junction block 36 and safety pin 50 prevents the barb pusher assembly 46 from sliding further into the junction block 36 prematurely. The barb pusher assembly 46 serves as a means to push the barb 44 into the inlet tube and seal the IID 23. An exemplary IID 23 is shown in FIGS. 1B, 1C, and 2B.

In FIG. 3 is shown a perspective view of a base 22. The base 22 has a base surface loft 60 (also see alternate view in FIG. 5), a base bottom surface 62 and a base wall 64 therearound. Base wall 64 includes base inner wall 66 and base outer wall 68, with an O-ring channel 70 formed in the top surface of the base wall 64. O-ring 26 is removably seated in O-ring channel 70. The base surface loft 60 and base wall 64 form a cavity 72 as shown. Base 22 also includes at least one junction block flange 76, a plurality of feet 78, a plurality of tab ramps 80, a tab ramp stop 82, and a snap lid stop 84. The junction block flange 76 is preferably located at the intersection of the base bottom surface 62 and the base outer wall 68. The junction block flange 76 has two flange sides 86, one flange base 88 between the flange sides 86, and notch 90 within flange base 88. The plurality of feet 78 extend outwardly from the base outer wall 68, and preferably are located at the intersection of the base bottom surface 62 and the base outer wall 68 and are uniformly distributed around the circumference of the base 22 as shown. In one embodiment, there are at least two feet 78. In another embodiment, there are four feet 78, but any convenient number may be used. Similarly, there are a plurality of tab ramps 80 located at the top edge of the base outer wall 68 extending outwardly from base outer wall 68 and uniformly distributed about the circumference of the base 22 as shown, with the first tab ramp 92 aligned with one flange side 86, and the last tab ramp 94 having a tab ramp stop 82. The tab ramps 80 increase in width in the clockwise direction such that, when the tab ramps 80 are engaged by snaps 156 (see FIG. 9) as the disk lid 28 (see FIG. 8) is rotated clockwise, simultaneously the O-ring 26 forms a seal between the disk lid 28 and base 22 such that fluids may not leak out of the loading device 20. The tab ramp stop 82 prevents excessive clockwise rotation, by limiting travel length, of the disk lid 28 and snap lid 30 (see FIG. 9), thereby preventing the snaps 156 of snap lid 30 from disengaging from the tab ramps 80 on base 22. In one embodiment, there are at least four tab ramps 80. In another embodiment, there are six tab ramps 80. Again, any convenient number may be used. The snap lid stop 84 is aligned with one flange side 86 at the top edge of the base outer wall 68. Furthermore, the snap lid stop 84 is positioned between the last tab ramp 94 and the junction block flange 76, such that the snap lid stop 84 limits counter-clockwise rotation of the snap lid 30 and disk lid 28, thereby preventing the snaps 156 on snap lid 30 from re-engaging the adjacent tab ramp 80 and enabling opening of the loading device 20 to gain access to the IID 23.

FIG. 4 shows a bottom perspective view of base 22. This view shows the base bottom surface 62 further has recessed base bottom 63 therein. The recessed base bottom 63 reflects the underside of base surface loft 60, and has base bottom surface 62 therearound. The handle 74 is fixedly attached to the recessed base bottom 63 along the length of the handle 74. Handle 74 extends downwardly from recessed base bottom 63. Handle 74 may be formed, for example by molding, into recessed base bottom 63. Handle 74 is useful for stabilizing the loading device 20, for example for stabilizing within the packaging, and providing features with which to grasp the loading device 20 when opening to retrieve the IID 23.

Figure 5:
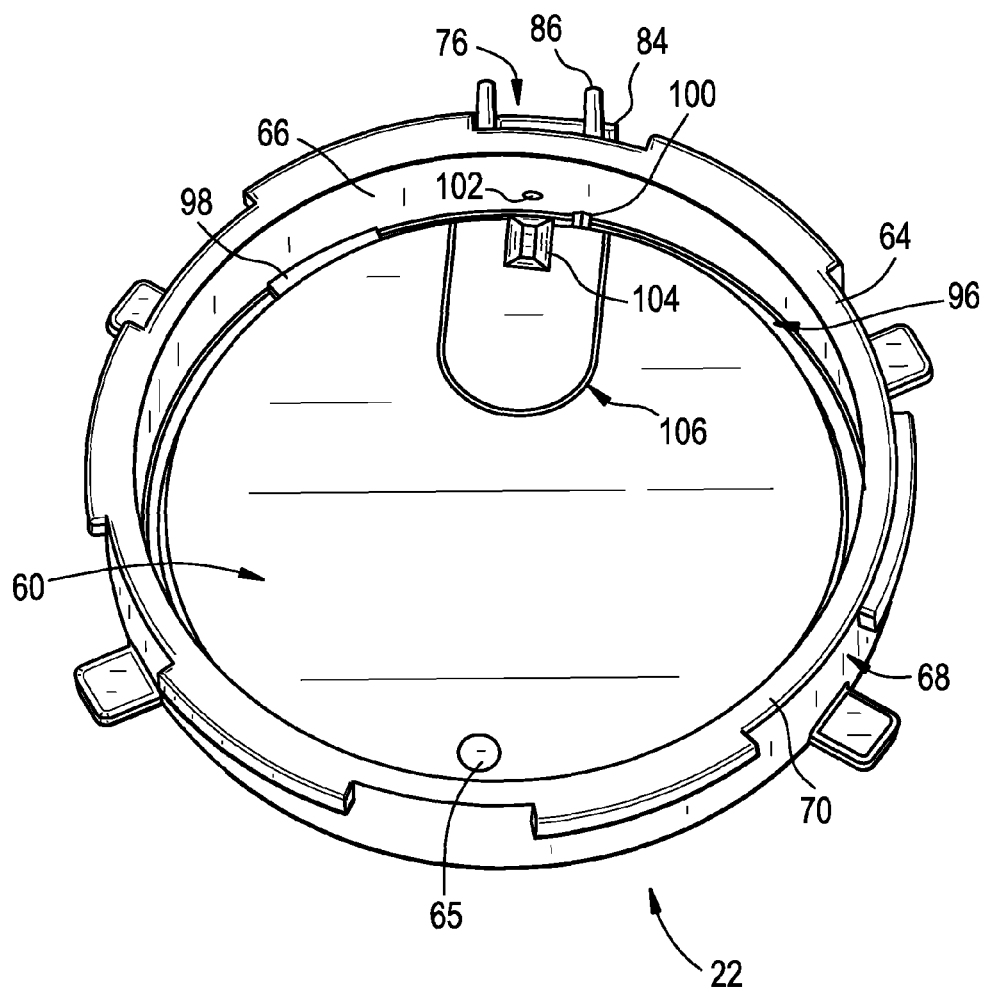
FIG. 5 is a top plan view of the base of FIG. 3.

FIG. 5 shows a top view of base 22 showing base surface loft 60 and base wall 64 therearound with a recessed blade ring channel 96 formed between the base surface loft 60 and base wall 64. Base wall 64 includes, base inner wall 66 and base outer wall 68, with an O-ring channel 70 formed in the top surface of the base wall 64. The base surface loft 60, while substantially flat, slopes down slightly with the high point 65 opposite the IID receiver 104. The slope of the base surface loft 60 is selected so that it maintains a uniform spacing with the lid floor bottom 144 of the disk lid 28 (see FIG. 8) when removably attached to base 22. The recessed blade ring channel 96 further has a blade ring stop 98, and a blade ring support 100. The blade ring stop 98 and blade ring support 100 are located in the recessed blade ring channel 96. The blade ring support 100 is approximately aligned with flange side 86 and snap lid stop 84. The blade ring stop 98 is positioned in the recessed blade ring channel 96, such that the blade ring end 116 (shown in FIG. 6) sits against the blade ring stop 98 and the blade end 118 sits on the blade ring support 100. The base wall 64 has an inlet tube conduit 102 on the base inner wall 66 and exiting on the base outer wall 68 (not shown). The inlet tube conduit 102 is approximately centered on the base wall 64 above the junction of the base wall 64 and the recessed blade ring channel 96, and within the junction block flange 76. Inlet tube conduit 102 is positioned on the base wall 64 such that when the IID 23 is seated on the base surface loft 60, the inlet tube of the IID 23 extends through inlet tube conduit 102 and into the junction block 36 (see FIG. 2B). The base surface loft 60 also has an IID receiver 104 on the base surface loft 60 and in line with the inlet tube conduit 102. The IID receiver 104 is a cut out that provides relief (or clearance space) for the attachment point between the inlet tube of the IID 23 and the cell pouch of the IID 23 such that the inlet tube of the IID 23 is not compressed during assembly of the loading device 20. The IID assembly aid 106 identifies the outline of the IID 23 as it sits on the base surface loft 60. The inlet tube of IID 23 (see FIG. 1B) extends through the inlet tube conduit 102 and the proximal end of the cell pouch of the IID 23 (see FIG. 1C) sits in the IID receiver 104.

Base 22 may be made by any known manner, but conveniently may be made in one piece using methods known to those of skill in the art of manufacturing plastic parts. The base 22 may be prepared from polymers suitable for medical use, such as medical grade polymers. The polymer should be rigid to maintain shape, withstand vacuum or pressure, moldable, translucent, and sterilizable. Suitable polymers, such as thermoplastic polymers, include but are not limited to polycarbonate, acrylonitrile butadiene styrene, polypropylene, polymethylmethacrylate, and the like. In one embodiment, the polymer is polycarbonate. The base 22 may be produced using various known methods in the art, including but not limited to molding, machining, and rapid prototyping such as, stereolithography, selective laser sintering, and the like.

Figure 6:
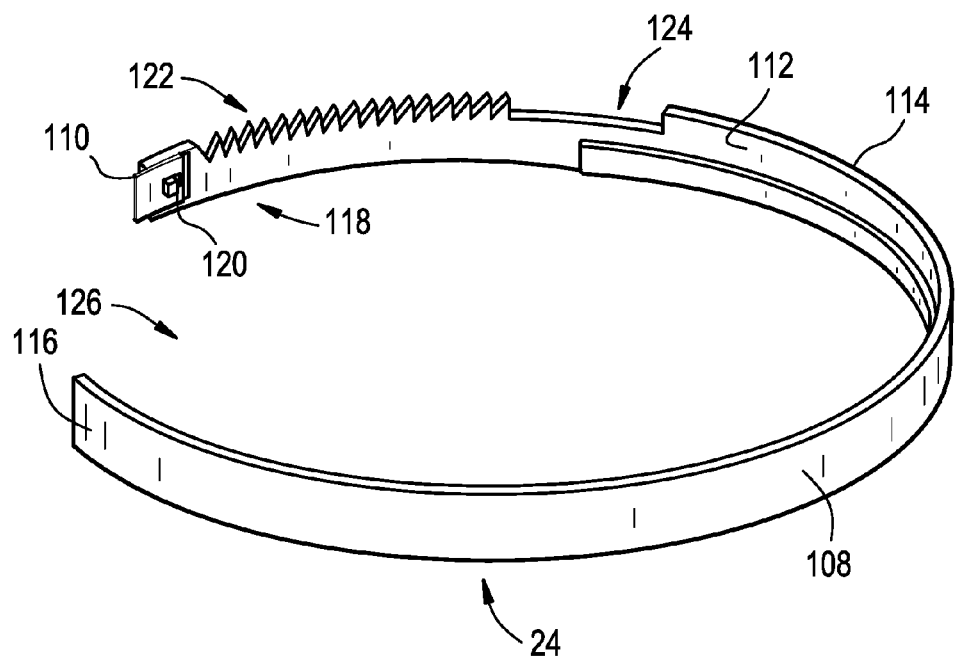
FIG. 6 is a top perspective view of a blade ring assembly of the device of FIG. 1A.

FIG. 6 depicts blade ring assembly 24 that is a semi-circular, flexible structure that includes blade ring 108 and blade 110. Blade ring 108 has a blade ring wall 112, a top edge 114, a blade ring end 116, and a blade end 118. The blade ring 108 terminates at one end in blade post 120 and at the other, in blade ring end 116. Adjacent to blade post 120 and positioned in top edge 114 are teeth 122 that end at spacer 124, adjacently located to teeth 122. The blade end 118 may be tapered for flexibility. Furthermore, blade ring assembly 24 has a blade ring opening 126.

The blade ring assembly 24 is prepared from two parts, a blade 110 and a blade ring 108. The blade 110 is made from a corrosion resistant material of sufficient rigidity with which to cut. In one embodiment, the blade 110 is made from surgical grade steel. The blade 110 is designed and custom made using known machining and grinding methods to produce a cutting edge. The blade ring 108 is prepared in one piece similarly to the base 22. The blade ring 108 and blade 110 may be assembled by a process known in the art as heat staking, where the blade 110 is slid onto the blade post 120 and then the blade post 120 is melted to secure the blade 110 to the blade ring 108. Heat staking is performed at a temperature sufficient to melt the blade post 120. Alternately, the blade 110 may be overmolded into the blade ring 108 or mechanically attached using snap features and the like. In another embodiment, the blade 110 is eliminated entirely and the cutting edge is applied to the blade end 118 of the blade ring 108 itself.

Figure 7:
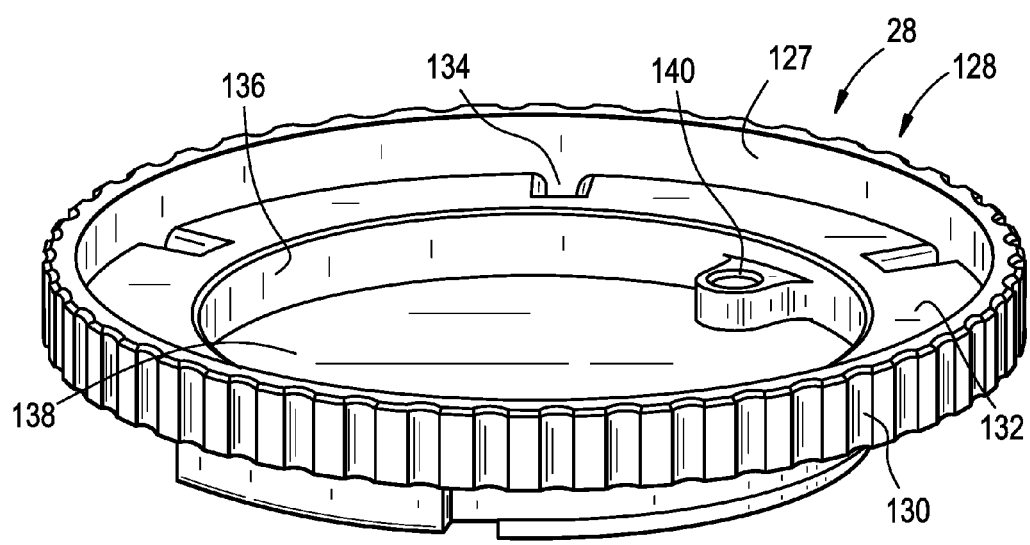
FIG. 7 is a top perspective view of a disk lid of the device of FIG. 1A.
Figure 8:
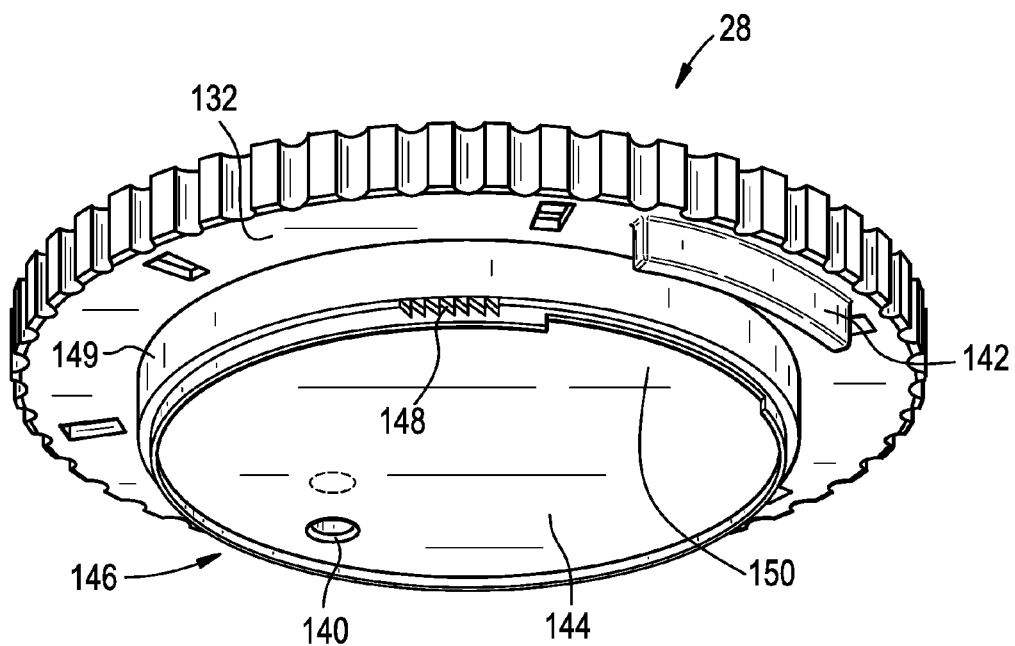
FIG. 8 is a bottom perspective view of the disk lid of FIG. 7.

FIGS. 7 and 8 show a top view and bottom view of a disk lid 28, respectively. The top view of the disk lid 28 shows a disk lid outer wall 128 having a plurality of grooves 130 therein, and a flange 132 extending inwardly from inner surface 127 of disk lid outer wall 128. Flange 132 has a plurality of snap lid holes 134 therein. In one embodiment, there are at least four snap lid holes 134. In another embodiment, there are six snap lid holes 134. While any number of snap lid holes 134 can be envisioned, the number of snap lid holes 134 should be equivalent to the number of snaps 156 on snap lid 30. Inner floor wall 136 extends downwardly from flange 132 and connects flange 132 terminating at lid floor 138 that extends inwardly from inner floor wall 136. A luer fitting receiver 140 extends upwardly from lid floor 138 and is adjacent to inner floor wall 136. The bottom view of the disk lid 28 as seen in FIG. 8 shows the junction block retention feature 142, which is a flange extending downwardly from the under surface of flange 132. Also shown is lid floor bottom 144 having a blade ring retainer 146 aligned with inner floor wall 136 (see FIG. 7) and extending downwardly from lid floor bottom 144. Furthermore, the blade ring retainer 146 has a cut out 150 aligned with the junction block retention feature 142 to provide relief for the inlet tube of IID 23. When the loading device 20 is assembled, blade ring retainer 146 connects slidably with blade ring wall 112 thereby ensuring that blade ring assembly 24 stays within the recessed blade ring channel 96 and also ensuring that lid teeth 148 engage teeth 122 on the blade ring assembly 24. Lid teeth 148 are positioned adjacent to cut out 150 and extend downwardly at the intersection of the outer floor wall 149 and the lid floor bottom 144. The lid teeth 148 connect ratchetedly with the teeth 122 on blade ring assembly 24 when the disk lid 28 is rotated clockwise, and snaps 156 on snap lid 30 engage tab ramps 80 of base 22. The lid teeth 148 interlock with teeth 122 when the disk lid 28 is rotated counter-clockwise, which then moves the blade ring assembly 24 counter-clockwise and enables the cutting of the inlet tube of IID 23 simultaneously. An opening for the luer fitting receiver 140 is also shown in lid floor bottom 144. The lid floor bottom 144 while substantially flat slopes down to a desired degree with the high point at the luer fitting receiver 140 opposite the cut out 150. The degree of slope of the lid floor bottom 144 preferably is sufficient to encourage air bubbles toward the luer fitting receiver 140 on the disk lid 28 such that the bubbles may be removed.

Figure 9:
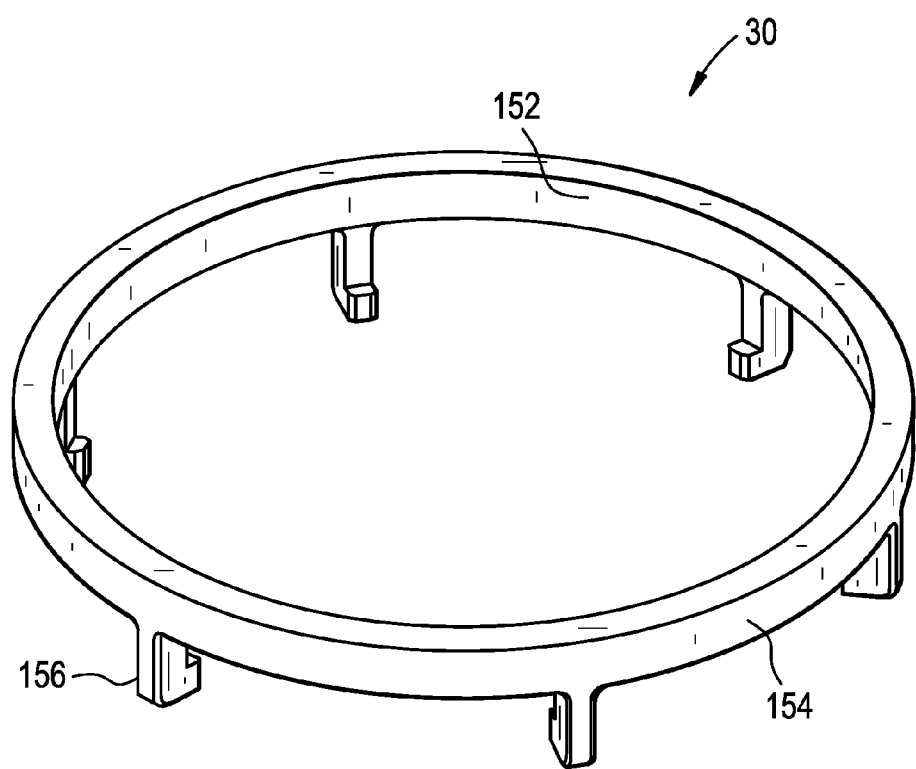
FIG. 9 is a top perspective view of a snap lid of the device of FIG. 1A.

FIG. 9 shows a perspective view of snap lid 30. Snap lid 30 is a ring member 152 having a ring outer wall 154, and a plurality of snaps 156 protruding downwardly from one surface of the ring. In one embodiment, there are at least four snaps 156. In another embodiment, there are six snaps 156. In yet another embodiment, the number of snaps 156 is equal to the number of snap lid holes 134, which is equal to the number of tab ramps 80. The snaps 156 are configured to be complementary to and fit through the snap lid holes 134 on disk lid 28 and removably engage corresponding tab ramps 80 on base 22. The tab ramps 80 are engaged by snaps 156 as the disk lid 28 is rotated clockwise; simultaneously the O-ring 26 forms a seal between the disk lid 28 and base 22 such that fluids may not leak out of the loading device 20.

A side view of a junction block 36 is shown in FIG. 10. The junction block 36 has a pusher channel 158, that tapers into a barb plug channel 160, that further narrows into a barb channel 162, which then widens into the inlet tube channel 164, that together extend through the length of the junction block 36. A second luer fitting 166 connects downwardly into the barb channel 162. The pusher channel 158 also has two pin conduits extending horizontally through the width of the junction block 36. The retainer pin conduit 168 is proximal to the safety pin conduit 170 and both pin conduits are located adjacent to the pusher channel opening 172. There are two tabs located at the distal end of the junction block 36. The locking tab 174 is on the top side of the junction block 36 and extends upwardly. The latch tab 176 is on the bottom side of the junction block 36 and extends downwardly, as shown. Junction block 36 is fixedly attached to base 22 by disk lid 28. Latch tab 176 is inserted into notch 90 in flange base 88 (see FIG. 3). Junction block seal 38 is located between junction block 36 and base 22, and within junction block flange 76. Junction block seal 38 forms a compression seal between junction block 36 and base 22. Second luer cap 40 is removably attached to the second luer fitting 166 on junction block 36 (see FIGS. 2A and 2B). Locking tab 174 is engaged by junction block retention feature 142 when the disk lid 28 is rotated clockwise, and, and snaps 156 on snap lid 30 engage tab ramps 80 of base 22. The tab ramp stop 82 prevents excessive clockwise rotation of the disk lid 28 and snap lid 30, thereby preventing the snaps 156 of snap lid 30 from disengaging from the tab ramps 80 on base 22. Similarly, snap lid stop 84 limits counter-clockwise rotation of the snap lid 30 and disk lid 28, such that the snaps 156 on snap lid 30 do not re-engage the adjacent tab ramp 80 and prevent opening of the loading device 20 when the loading device 20 is being opened to gain access to the IID 23.

The disk lid 28, snap lid 30, and junction block 36 are all prepared according to the methods described above for base 22, each as one whole part.

Figure 11:
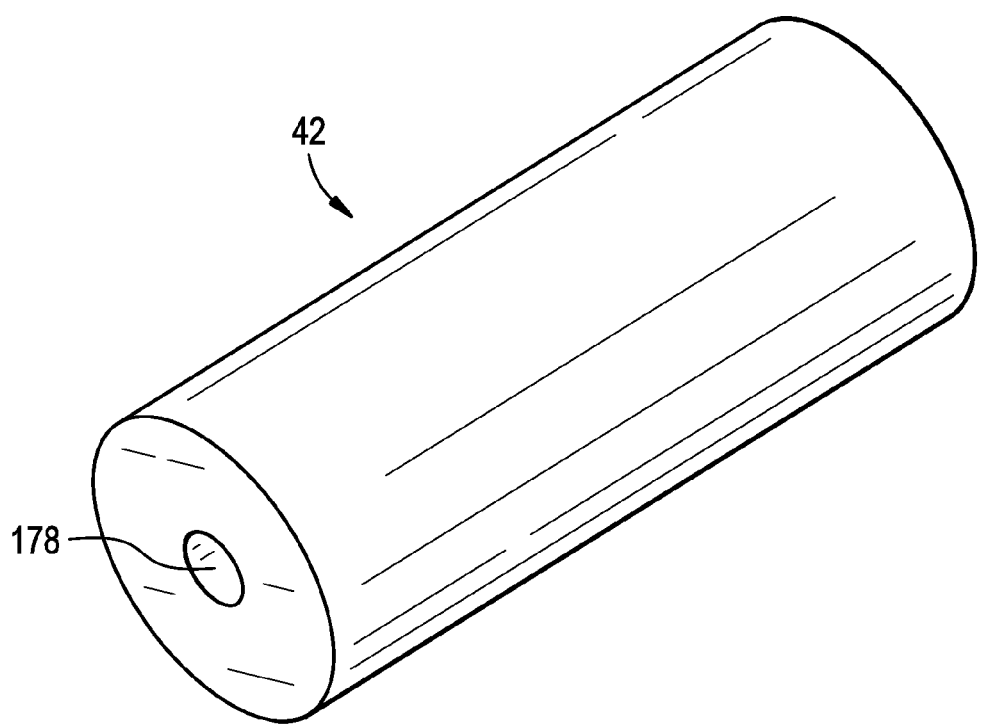
FIG. 11 is a side perspective view of a barb plug of the device of FIG. 1A.

A perspective view of a barb plug 42 is shown in FIG. 11. The barb plug 42 has a barb receiver channel 178 that runs the length of the barb plug 42. The barb plug 42 holds the barb 44 within the barb receiver channel 178 and is removably located within barb plug channel 160 of junction block 36 (see FIG. 10). The barb plug 42, as well as the O-ring 26, and junction block seal 38 are all prepared from compliant materials, for example elastomers, that will conform to the space provided and prevent any fluid leaking from the loading device 20. In one embodiment, the elastomer may be polyurethane or a silicone elastomer. In another embodiment, the elastomer is a silicone elastomer. The elastomeric materials are also able to undergo sterilization without being degraded or deformed.

Figure 12:
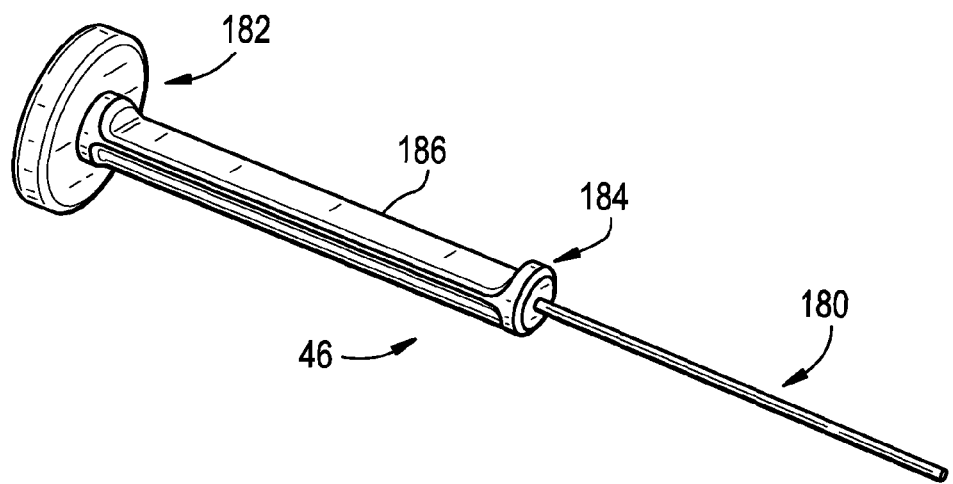
FIG. 12 is a side perspective view of a barb pusher assembly of the device of FIG. 1A.

A perspective view of a barb pusher assembly 46 is shown in FIG. 12. The barb pusher assembly 46 has wire pusher 180 on the distal end and plunger 182 on the proximal end. The plunger 182 has a plunger stop 184 and a guide plane 186. Safety pin 50 is inserted into safety pin conduit 170 on junction block 36. The barb pusher assembly 46 is inserted into the pusher channel opening 172 of junction block 36 with guide plane 186 facing upward until the plunger stop 184 meets the safety pin 50. The retainer pin 48 is then inserted into the retainer pin conduit 168, on the proximal side of plunger stop 184, thereby preventing the barb pusher assembly 46 from falling out of the junction block 36 (see also FIG. 10).

The barb pusher assembly 46 is designed and constructed with adequate column strength to advance and seat the barb 44 into the IID 23. The wire pusher 180 is prepared from corrosion resistant, medical grade metal and is of suitable strength to place the barb 44 without deformation. Suitable metals include, but are not limited to stainless steel, cobalt-chromium alloys, titanium, and titanium alloys. In one embodiment, the metal is stainless steel. The plunger 182 may be made from polymers suitable for medical use, for example the polymer should be rigid to maintain shape and sterilizable. Suitable polymers include, but are not limited to polycarbonate, acrylonitrile butadiene styrene, polypropylene, polymethylmethacrylate, and the like. In one embodiment, the polymer is polycarbonate. The barb pusher assembly 46 may be manufactured using known insert molding methods or other processes, such as machining.

The retainer pin 48 and safety pin 50 are prepared from corrosion resistant, medical grade metal. Suitable metals include, but are not limited to stainless steel, cobalt-chromium alloys, titanium, and titanium alloys. In one embodiment, the metal is stainless steel.

The barb 44 may be prepared in a suitable shape and from suitable materials that will provide a seal to prevent cells or cell clusters or media from leaking from the inlet tube of the IID 23. Suitable materials include, but are not limited to elastomers or corrosion resistant, medical grade metals. Suitable elastomers include, but are not limited to polyurethane or silicone elastomers. Suitable metals include, but are not limited to stainless steel, cobalt-chromium alloys, titanium, and titanium alloys. In one embodiment, the metal is titanium.

The loading device 20 is assembled by first installing an IID 23 into a base 22, inserting the inlet tube through the inlet tube conduit 102 from the inside of the base 22. The IID 23 is aligned with the IID assembly aid 106 and held in place while the junction block seal 38 is installed over the inlet tube. The junction block seal 38 is advanced over the inlet tube until the junction block seal 38 is against the base outer wall 68 of the base 22. An ultraviolet light activated adhesive is then applied to the inlet tube and the inlet tube is inserted into the inlet tube channel 164 of junction block 36. Latch tab 176 on junction block 36 is then engaged with notch 90 in flange base 88 of the base 22. A UV light source is then activated shining through the side of the clear plastic junction block 36 to cure the UV adhesive within while the components are held in place. The UV adhesive secures the inlet tube within the inlet tube conduit 102, thereby holding the IID 23 in place during the cell loading process. Suitable UV adhesives are solvent free, flexible, rapid curing, and compatible with the polymer components of the loading device 20. Blade ring assembly 24 is then inserted in the recessed blade ring channel 96 with the blade ring end 116 against the blade ring stop 98 and the blade end 118 on the blade ring support 100. The O-ring 26 is disposed in the O-ring channel 70. The disk lid 28 is then secured to the base 22 using the snap lid 30. The snaps 156 on snap lid 30 feed through the snap lid holes 134 on disk lid 28, the snap lid 30 is recessed in the disk lid 28, and snaps 156 engage the tab ramps 80 while rotating the disk lid clockwise onto base 22. The disk lid 28 is turned clockwise such that the lid teeth 148 ratchetedly engage the teeth 122 on the blade ring assembly 24 and the junction block retention feature 142 engages locking tab 174 thereby securing the junction block 36 in place within junction block flange 76. The barb 44 is loaded into the barb receiver channel 178 within barb plug 42 and barb plug 42 is seated into the barb plug channel 160. The barb pusher assembly 46 is then inserted into the pusher channel 158 of junction block 36 with the wire pusher 180 sliding into the barb receiver channel 178 within the barb plug 42. The barb pusher assembly 46 is held in place within the junction block 36 by placing the safety pin 50 in safety pin conduit 170 and placing the retainer pin 48 in retainer pin conduit 170. The safety pin 50 prevents premature placement of the barb 44 in the inlet tube of the IID 23 and the retainer pin 48 prevents the barb pusher assembly 46 from coming out of the junction block 36. Lastly, the loading device 20 is closed using first and second luer caps 34 and 40, to close the first and second luer fittings 32 and 166, respectively.

Once assembled, the loading device 20 is sterilized and ready to use. The loading device 20 is sterilized using techniques known to those of skill in the art of sterilization, such as gamma sterilization, e-beam sterilization, and ethylene oxide sterilization. The loading device 20 may be sterilized using any of the previously described techniques, however since the IID 23 is sterilized in the loading device 20 the materials used to prepare the IID 23 must be considered when selecting a sterilization technique. In one embodiment, the loading device 20 is sterilized using ethylene oxide sterilization.

The sterile loading device 20 is useful for loading cells, cell clusters, or media into the IID 23. All cell loading steps are performed using aseptic sterile techniques in a laminar flow hood to maintain sterility and reduce the chances of contamination. The cell pouch of the IID 23 is prepared from semipermeable membranes that may be either hydrophilic or hydrophobic in nature. If the semipermeable membranes are hydrophilic the following wetting step may be optional, however if the semipermeable membranes are hydrophobic the following wetting step is required to enhance the wetting of the IID 23. The wetting of the IID 23 is as follows. Sterile saline is introduced through the first luer fitting 32 on the disk lid 28. The entire cavity 72 of the loading device 20 is filled with saline from an elevated (<3 meters) container without pumps or pressure. Care must be taken not to over pressurize the IID 23. Next, a syringe containing alcohol is then attached to the second luer fitting 166 on the junction block 36. Suitable alcohols include, but are not limited to ethanol and isopropanol, and mixtures thereof. In one embodiment, the alcohol is ethanol. In another embodiment, the alcohol is isopropanol in a aqueous solution with up to 40% of water by volume. The alcohol is injected into the junction block 36 which then enters the inlet tube and then wets the cell pouch (semipermeable membranes) of the IID 23. The system is allowed to equilibrate, allowing a sufficient time for the semipermeable membranes to wet with alcohol, such as for about 3 minutes. At least 1 mL of fluid is removed through the second luer fitting 166 on junction block 36 to remove the excess alcohol. The syringe is then removed from the second luer fitting 166 on junction block 36. The saline source is moved from the first luer fitting 32 on the disk lid 28 and transferred to the second luer fitting 166 on the junction block 36. A vacuum line is subsequently attached to the first luer fitting 32 on the disk lid 28. A vacuum pressure of up to 200 mm Hg is applied and maintained until at least about 40 mL of saline passes through the second luer fitting 166 on junction block 36, thereby thoroughly rinsing the IID 23 and loading device 20 to remove residual alcohol. All lines are removed from the first and second luer fittings 32 and 166 and they are sealed with first and second luer caps 34 and 40, respectively. The loading device 20 is then allowed to sit (12-18 hours) at room temperature.

Subsequently, a vacuum line is attached to the first luer fitting 32 on the disk lid 28 and a cell and media source is attached to the second luer fitting 166 on junction block 36. A vacuum of up to 200 mm Hg is applied until the cell and media source is exhausted. The safety pin 50 is removed from the junction block 36 and the barb pusher assembly 42 is pushed until the distal face of plunger 182 contacts the proximal face of the junction block 36. This motion simultaneously advances the plunger stop 184 causing compression of the barb plug 42 and the wire pusher 180 pushes the barb 44 through barb channel 162 on the junction block 36, into the inlet tube of the IID 23 and is deployed, thereby sealing the inlet tube of IID 23. Upon releasing the plunger 182, the barb pusher assembly 46 springs back slightly, such that the wire pusher 180 does not extend beyond the distal end of junction block 36 and is out of the pathway of the blade 110 of blade ring assembly 24. The loading device 20 is then packaged for transport in a manner which preserves sterility of the exterior of the assembly. In one embodiment, the loading device 20 is stabilized in a thermoform mold by snapping the feet 78 within the mold, which is then followed by enclosing in a sterile package. The packaged loading device 20 is then transported to the point of use while maintaining sterility of the assembly. In one embodiment, the packaged loading device 20 is transported under suitable conditions to maintain viability of the cells therein. A suitable shipping temperature may be determined by the skilled artisan and is dependent upon the cell. The loading device 20 is introduced into the sterile field and removed from sterile packaging. The loading device 20 is gripped on the grooves 130 on the disk lid outer wall 128 of the disk lid 28 with one hand and the other hand grips the handle 74. The disk lid 28 is twisted counter-clockwise thereby rotating the blade ring assembly 24 and cutting the inlet tube flush with the end of the cell pouch of IID 23, while simultaneously removing the disk lid 28. The IID 23 then may be presented to the surgeon for implantation.

Figure 13:
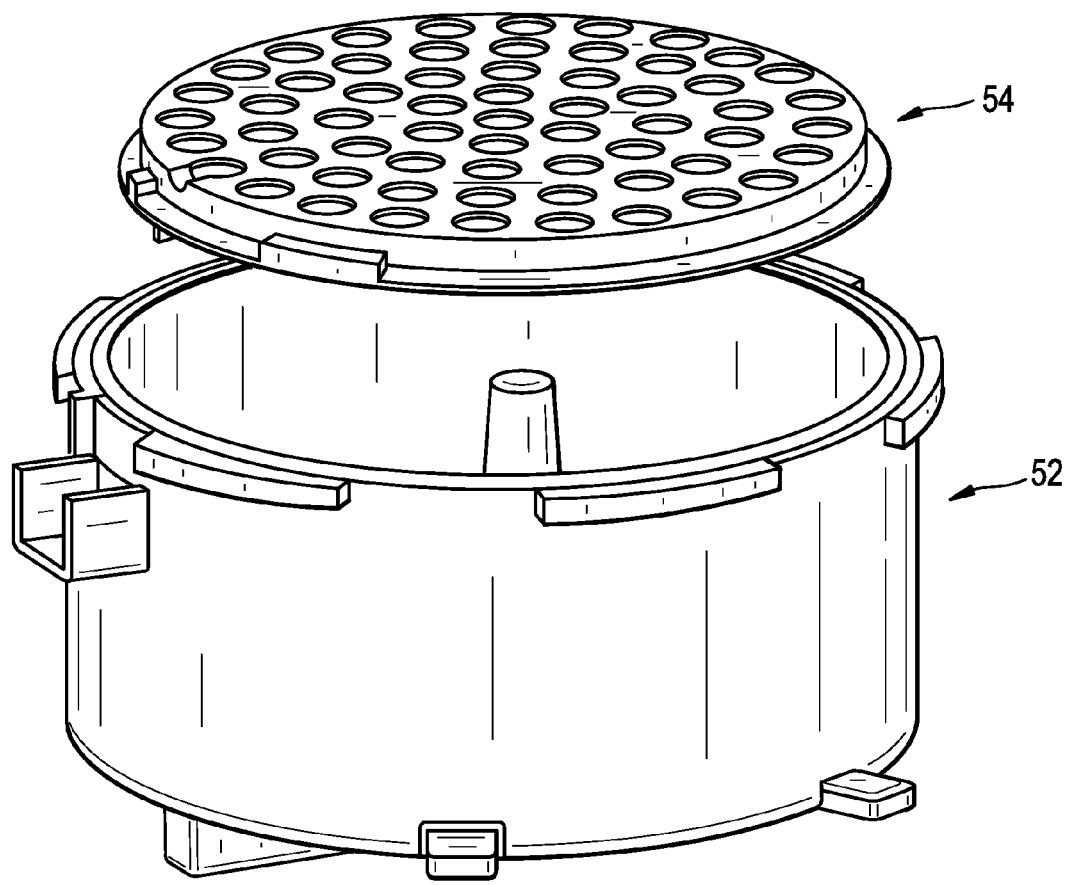
FIG. 13 is an exploded view of an alternate embodiment of the base of FIG. 3 with support plate.

The loading device 20 may be adapted for the size of the IID 23. More specifically, the loading device 20 may be adapted to hold more media to meet the needs of the increased number of cells in a larger IID 23. An exploded view of base 52 and support plate 54 is shown in FIG. 13. Base 52 is deeper as shown in comparison to base 22 described above, to accommodate more media. Due to the depth of base 52 an additional component, a support plate 54, is required and described in detail below.

Figure 14:
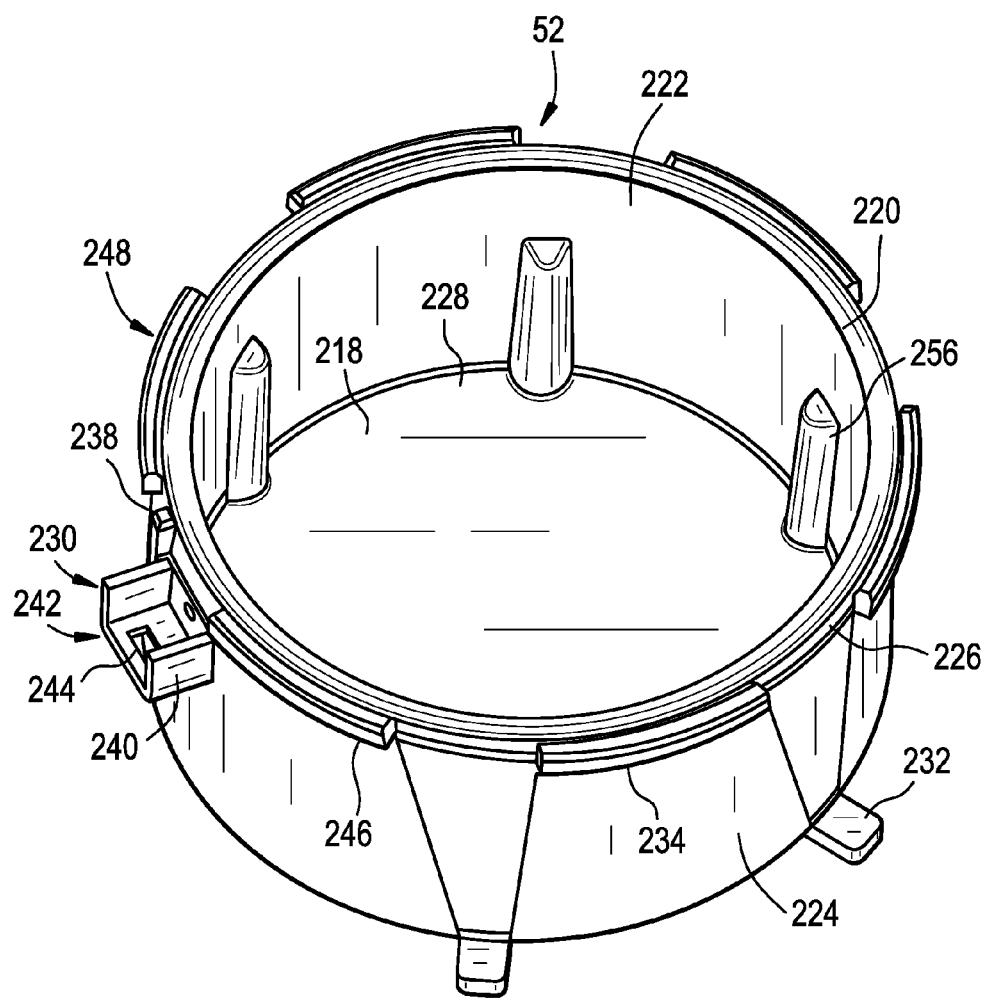
FIG. 14 a top perspective view of a base of FIG. 13.
Figure 15:
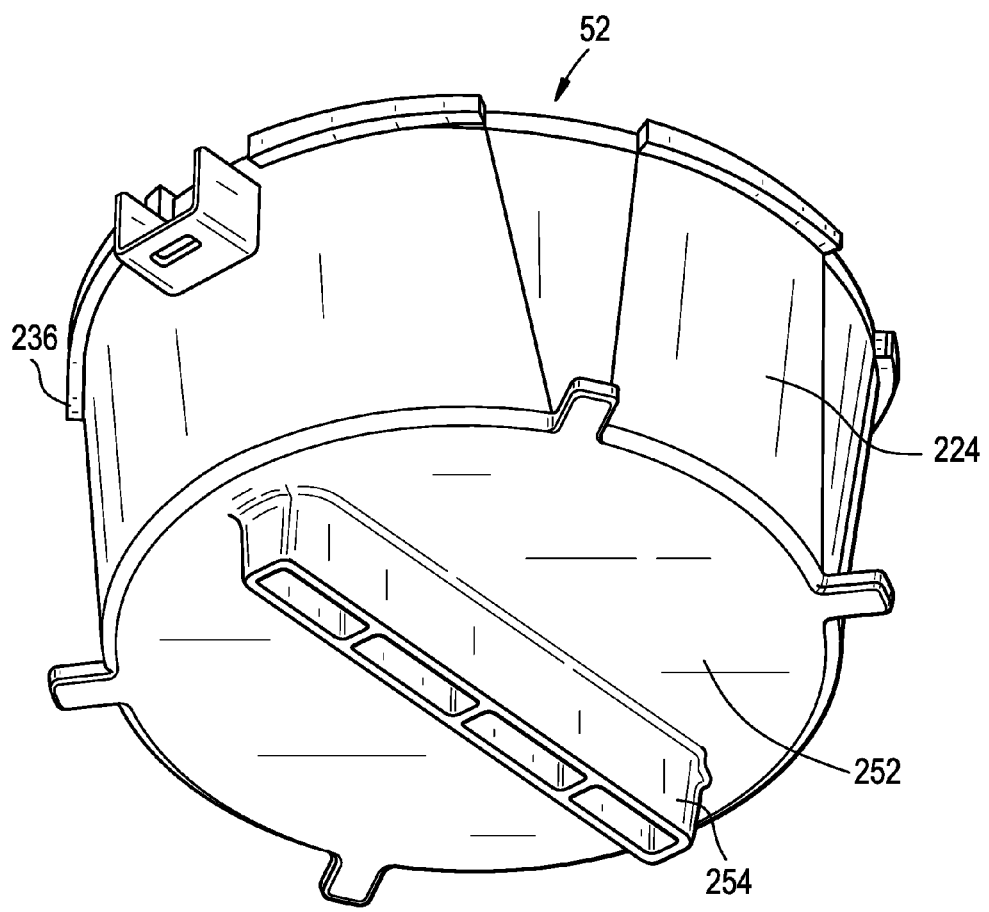
FIG. 15 is a bottom perspective view of the base of FIG. 13.
Figure 16:
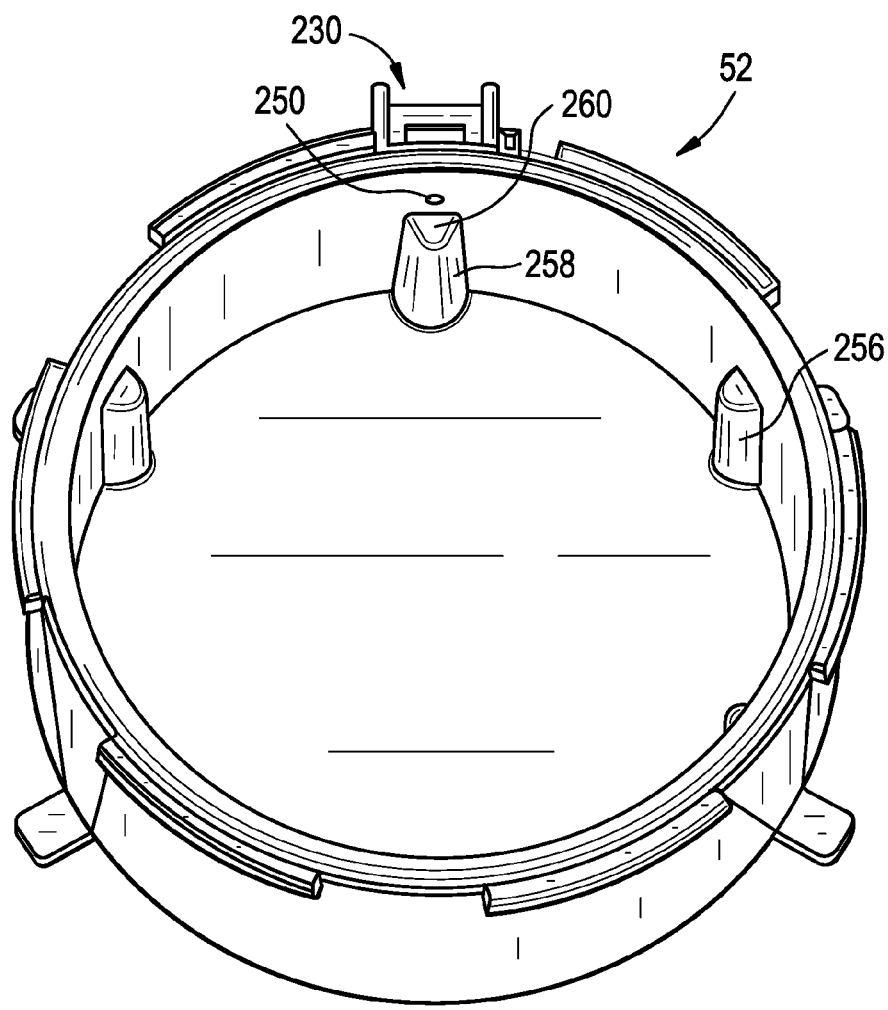
FIG. 16 is an alternate top perspective view of a base of FIG. 13.

Several views of base 52 are shown in FIGS. 14, 15, and 16. Base 52 has base surface 218 and base wall 220 therearound. The base surface 218 and base wall 220 form a cavity 228 as shown. Base wall 220 includes, base inner wall 222 and base outer wall 224, with an O-ring channel 226 formed in the top surface of the base wall 220. The base wall 220 has an inlet tube conduit 250 on the base inner wall 222 and exiting on the base outer wall 224 (see FIG. 16). Inlet tube conduit 250 is positioned on the base wall 220 such that when the IID 23 is seated on the support plate 54, the inlet tube of the IID 23 extends through the inlet tube conduit 250. Base 52 also includes at least one junction block flange 230, a plurality of feet 232, a plurality of tab ramps 234, a tab ramp stop 236, and a snap lid stop 238. The junction block flange 230 is located below the top edge of base outer wall 224 and extending outwardly with inlet tube conduit 250 approximately centered within. The junction block flange 230 has two flange sides 240, one flange base 242 between the flange sides 240, and notch 244 within flange base 242. The plurality of feet 232 extend outwardly from the base outer wall 224, and preferably are located at the intersection of the base bottom surface 252 (see FIG. 15) and the base outer wall 224 and are uniformly distributed around the circumference of the base 52 as shown. In one embodiment, there are at least two feet 232. In another embodiment, there are four feet 232, but any convenient number may be used. Similarly, there are a plurality of tab ramps 234 located at the top edge of the base outer wall 224 extending outwardly from base outer wall 224 and uniformly distributed about the circumference of the base 52 as shown, with the first tab ramp 246 aligned with one flange side 240 and the last tab ramp 248 having a tab ramp stop 236 extending downwardly (see FIG. 15). The tab ramps 234 increase in width in the clockwise direction such that when the tab ramps 234 are engaged by snaps 156 of snap lid 30 as the disk lid 28 is rotated clockwise; simultaneously the O-ring 26 forms a seal between the disk lid 28 and base 52 such that fluids may not leak out of the base 52. The tab ramp stop 236 (see FIG. 15) prevents excessive clockwise rotation of the disk lid 28 and snap lid 30, thereby preventing the snaps 156 of snap lid 30 from disengaging from the tab ramps 234 on base 52. In one embodiment, there are at least four tab ramps 234. In another embodiment, there are six tab ramps 234. The snap lid stop 238 is aligned with one flange side 240 and the top edge of the base outer wall 224. Furthermore, the snap lid stop 238 is positioned between the last tab ramp 248 and the junction block flange 230, such that the snap lid stop 238 limits counter-clockwise rotation of the snap lid 30 and disk lid 28, thereby preventing the snaps 156 on snap lid 30 from re-engaging the adjacent tab ramp 234 and enabling opening of the loading device 20 when the loading device 20 is being opened to gain access to the IID 23.

An alternate top perspective view of base 52 is shown in FIG. 16. Base 52 has a plurality of support ribs 256 extending upwardly from base surface 218 and connected fixedly to base surface 218 and base inner wall 222. The number of support ribs 256 is in an amount sufficient to hold support plate 54 elevated in the base 52 without tilting and the height of support ribs 256 are such that the IID 23 is held in line with inlet tube conduit 250. The support ribs 256 are uniformly distributed around the circumference of the base 52 as shown, beginning with first support rib 258 located under inlet tube conduit 250 and having support rib notch 260 molded into the top surface of first support rib 258. In one embodiment, there are at least four support ribs 256. In another embodiment, there are at least six support ribs 256 but any convenient number may be used.

FIG. 15 shows a top perspective view of base 52. Handle 254 may be formed, for example by molding, into base bottom surface 252. Handle 254 is useful for stabilizing the loading device 20, for example for stabilizing within the packaging, and providing features with which to grasp the loading device 20 when opening to retrieve the IID 23.

Figure 17:
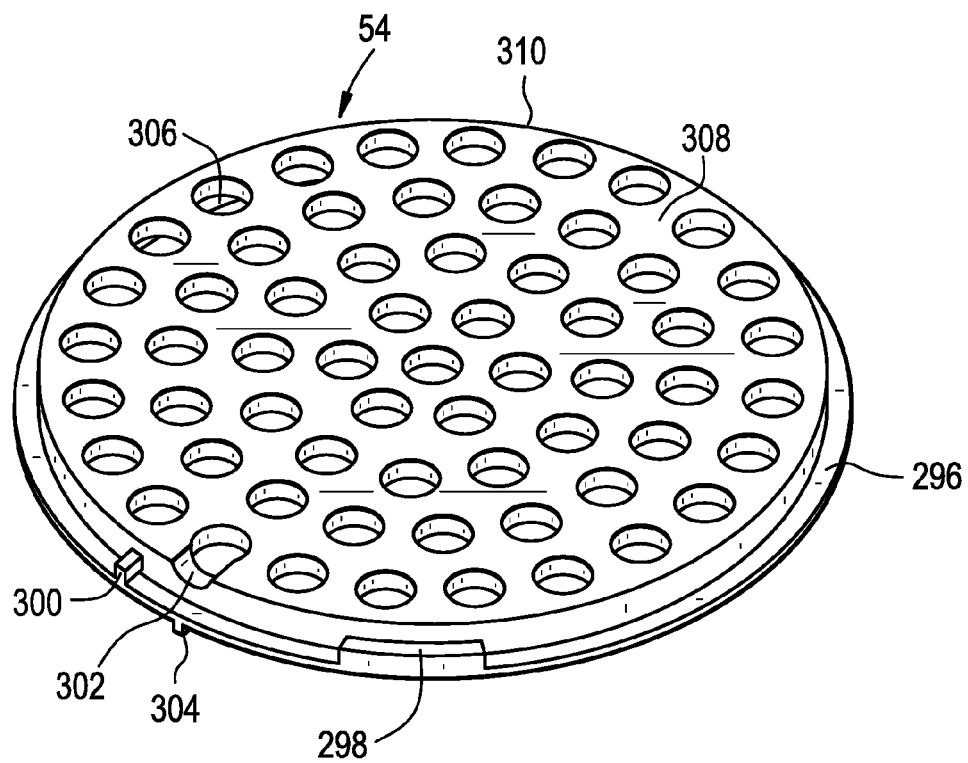
FIG. 17 is a top perspective view of a support plate of FIG. 13.

A top perspective view of support plate 54 is shown in FIG. 17. Support plate 54 removably connects with base 52 by resting on support ribs 256 and against base inner wall 222. Support plate tab 304, located on bottom side of support plate 54, removably seats in support rib notch 260 on first support rib 258. Support plate 54 has plate surface 308 and blade ring channel 296 therearound, which further has a blade ring stop 298, and a blade ring support 300 within blade ring channel 296. The blade ring support 300 is approximately aligned with flange side 240 and snap lid stop 238 when loading device 20 is assembled. The blade ring stop 298, is positioned in the blade ring channel 296, such that the blade ring end 116 sits against the blade ring stop 298 and the blade end 118 sits on the blade ring support 300. Plate surface 308, while substantially flat, slopes down from high point 310 and angled toward IID receiver 302. The slope is selected so that it maintains a uniform spacing with the lid floor bottom 144 of the disk lid 28, when the loading device 20 is assembled. IID receiver 302 is located on plate surface 308 and is a cut out that provides relief (or clearance space) for the attachment point between the inlet tube of the IID 23 and the cell pouch of the IID 23 such that the inlet tube of the IID 23 is not compressed during assembly of the loading device 20. Support plate 54 has a plurality of plate holes 306 vertically through the height of support plate 54. The plate holes 306 are selected as to sufficiently allow fluid and gas exchange above and below support plate 54, while supporting the IID 23 on plate surface 308.

The remainder of the loading device 20 components are assembled as previously described above for loading device 20.

The loading device 20 is useful to load an immune-isolation device ("IID") with cells or cell clusters while minimizing the opportunities for contamination due to manual manipulation. Previously, the process for loading cells, cell clusters, media, or wetting agents into the device required the user to manually handle the IID 23, including directly touching the inlet tube or the cell pouch of the IID 23. The invention allows the user to handle the loading device 20 without ever touching the IID 23, until the IID 23 is purposely removed from the loading device 20 for implantation. The IID 23 is not removed from the loading device 20 until the point of use.

Furthermore, the loading device 20 is also useful as the packaging for the IID 23. The feet 78 (or 232) secure the loading device 20 in the secondary packaging. At the point of use, the loading device 20 is removed from the secondary packaging, the disk lid 28 is gripped and turned counter-clockwise which simultaneously opens the loading device 20 and the blade 110 trims the inlet tube of the IID 23 to be flush with the proximal end of the cell pouch of the IID 23 (not shown). The IID 23 is then carefully removed from the loading device 20 and implanted at the point of use.

EXAMPLES

Example 1

This example describes the use of the loading device 20 to load cells or cell clusters into the IID 23. A loading device 20 is assembled as described above and sterilized using ethylene oxide sterilization. All steps below are performed using aseptic sterile techniques in a laminar flow hood unless stated differently. First, the IID 23 is treated to enhance wetting of the IID 23. Sterile saline is introduced through the first luer fitting 32 on the disk lid 28. The entire cavity 72 of the loading device 20 is filled with saline from an elevated (<3 meters) container without pumps or pressure. Care must be taken not to over pressurize the IID 23. A syringe containing ethyl alcohol is then attached to the second luer fitting 166 on junction block 36. Ethanol is injected into the junction block 36 which wets the semipermeable membranes of the IID 23. The system is allowed to equilibrate for about 3 minutes then at least 1 mL of fluid is removed through second luer fitting 166 on junction block 36. The syringe is then removed from the second luer fitting 166 on junction block 36. The saline source is moved from the first luer fitting 32 on the disk lid 28 to the second luer fitting 166 on junction block 36 and simultaneously a vacuum line is attached to the first luer fitting 32 on the disk lid 28. A vacuum pressure of up to 200 mm Hg is applied and maintained until 40 mL of saline passes through the second luer fitting 166 on junction block 36. All lines are removed from the first and second luer fittings 32 and 166 and they are sealed with first and second luer caps 34 and 40, respectively. The loading device 20 then allowed to sit (12-18 hours) at room temperature.

Subsequently, a vacuum line is attached to the first luer fitting 32 on the disk lid 28 and a cell and media source is attached to the second luer fitting 166 on junction block 36. A vacuum of up to 200 mm Hg is applied until the cell and media source is exhausted. The safety pin 50 is removed from the junction block 36 and the barb pusher assembly 46 is pushed until the distal face of plunger 182 contacts the proximal face of the junction block 36. This motion simultaneously advances the plunger stop 184 causing compression of the barb plug 42 and the wire pusher 180 pushes the barb 44 through barb channel 162 on the junction block 36, into the inlet tube of the IID 23 and is deployed, thereby sealing the inlet tube of IID 23. Upon releasing the plunger 182, the barb pusher assembly 46 springs back slightly, such that the wire pusher 180 does not extend beyond the distal end of junction block 36 and is out of the pathway of the blade 110 of blade ring assembly 24. The loading device 20 is then packaged for transport in a manner which preserves sterility of the exterior of the assembly. The packaged loading device 20 is then transported to the point of use again while maintaining sterility of the assembly. The loading device 20 is brought into the sterile field and opened counter-clockwise to present the IID 23 for implantation. The act of opening the loading device 20 cuts the inlet tube of the IID 23 flush with the end of the cell pouch of IID 23 and allows the cell loaded IID 23 to be retrieved for implantation.

What is claimed is:

1. A system for loading immune-isolation devices comprising:
    a base having a base bottom surface and a base wall extending from the base bottom surface to form a cavity;
    an inlet conduit positioned on the base and extending there through into the cavity of the base;
    a disk lid removably attachable to the base to seal the cavity; and
    a blade having an edge slidably disposed within the cavity of the base;
    wherein the edge of the blade is configured to slide in front of the inlet conduit;
    wherein the system is configured to be vented;
    wherein the blade is disposed on an end of a blade assembly slidably located in the cavity of the base; and
    wherein the blade assembly is configured to interact ratchedly with the disk lid.

2. The system of claim 1 further comprising an opening in the disk lid.

3. The system of claim 1, wherein the blade assembly includes a first set of teeth and the disk lid includes a second set of teeth, and wherein the first set of teeth interlock with the second set of teeth.

4. The system of claim 1, wherein the blade assembly is semi-circular.

5. The system of claim 1, further comprising a snap lid shaped to be complimentary to the disk lid and containing a plurality of snaps which interlock with at least one feature on the base to secure the disk lid to the base.

6. The system of claim 5, wherein the at least one feature comprises ramps extending from the base wall, and wherein the plurality of snaps are generally hooked as to engage the at least one feature.

7. The system of claim 6, wherein the disk lid further comprises a plurality of snap holes configured to allow at least some of the plurality of snaps to extend there through before engaging the at least one feature.

8. The system of claim 1 further comprising a junction block having a first opening and a second opening wherein the first opening and second opening define a channel through the junction block, and wherein the first opening is configured to be coupled to the inlet conduit on an outside portion of the base wall.

9. The system of claim 8, wherein the channel comprises a plurality of portions, each of the plurality of portions of the channel having different diameters.

10. The system of claim 9, wherein a third opening intersects a first one of the plurality of portions of the channel.

11. The system of claim 10, wherein the junction block further comprises a first feature proximate to the first opening that interlocks with a second feature on the base wall.

12. The system of claim 10, wherein the junction block further comprises a first pin conduit and a second pin conduit configured to receive pins and are located proximate to the second opening of the junction block.

13. The system of claim 10 further comprising a barb having a shape complimentary to the first one of the plurality of portions, and wherein the barb is configured to be inserted through the channel of the junction block to create a seal in an immune-isolation device or the junction block.

14. The system of claim 13 further comprising a barb plug having a shape complimentary to a second one of the plurality of portions and having a barb channel proceeding through the barb plug, wherein the barb channel is complimentary to the barb.

15. The system of claim 14 further comprising a barb pusher comprising a plunger configured to advance the barb through the channel.

16. The system of claim 1, wherein the base further comprises a feature on the base bottom surface outside the cavity.

17. The system of claim 16, wherein the feature is configured to be gripped by a human hand or interlock with an outside feature during transportation.

18. The system of claim 1, wherein the base further comprises a plurality of ribs on the base wall inside the cavity.

19. The system of claim 18 further comprising a support plate configured to rest on the plurality of ribs.

20. The system of claim 19, wherein the support plate further comprises at least one opening.

21. The system of claim 1, wherein the base bottom surface is slanted or has a single high point.

22. The system of claim 1 further comprising an immune-isolation device comprising an inlet tube attached to a pouch, the inlet tube configured to be coupled the inlet conduit positioned on the base within the cavity.

* * * * *